United States Patent [19]

Belanger et al.

[11] Patent Number: 5,047,258
[45] Date of Patent: Sep. 10, 1991

[54] AQUEOUS SPRAY-COATING PROCESS

[75] Inventors: Raymond J. Belanger, Rensselaer; Gregg Stetsko, Bethlehem; Shrikant N. Pagay, Guilderland, all of N.Y.

[73] Assignee: Sterling Drug Inc., New York, N.Y.

[21] Appl. No.: 622,293

[22] Filed: Dec. 4, 1990

Related U.S. Application Data

[63] Continuation of Ser. No. 380,048, Jul. 14, 1989, abandoned.

[51] Int. Cl.$^5$ .............................................. A61K 9/32
[52] U.S. Cl. ...................................... 427/3; 424/471; 424/482; 427/12
[58] Field of Search ................... 427/3, 212; 424/471, 424/482

[56] References Cited

U.S. PATENT DOCUMENTS

| | | | |
|---|---|---|---|
| 4,572,833 | 2/1986 | Pedersen et al. | 424/482 |
| 4,606,909 | 8/1986 | Bechgaard et al. | 424/482 |
| 4,775,536 | 10/1988 | Patell | 424/471 |
| 4,800,087 | 1/1989 | Mehta | 424/482 |
| 4,816,264 | 3/1989 | Phillips et al. | 424/482 |

FOREIGN PATENT DOCUMENTS 58-109413  6/1983  Japan .

OTHER PUBLICATIONS

Eudragit L 30 D brochure, Röhm Pharma GmbH; undated, pp. 1–7.

Dechesne et al. "Study of the Application Conditions for Enterically Soluble and Gastroresistant Coatings Eudragit ® L30D." J. Pharm. Belg. 37, 273–282 (1982) (original and translation thereof).

Lehmann "Herstellung und Verwendung von Latices aus redespergierbaren Pulvern anionischer Acrylharze."*Acta Pharm. Tech.* 31,96–105 (1985).

Lehmann "Chemistry and Application Properties of Polymethacrylate Coating Systems" in *Aqueous Polymeric Coatings for Pharmaceutical Dosage Forms*, J. W. McGinity ed. Marcel Dekker 1989; pp. 153–245; 191–192.

Mehta "Processing and Equipment Considerations for Aqueous Coatings" in *Aqueous Polymeric Coatings for Pharmaceutical Dosage Forms*, J. W. McGinity ed.; Marcel Dekker 1989 pp. 256–302.

Ebey "A Thermodynamic Model for Aqueous Film-Coating"*Pharmaceutical Technology* 11, 40–50 (1987).

Reiland et al. "Aqueous Film-Coating Vaporization Efficiency", *Drug Development and Industrial Pharmacy* 9, 945–958 (1983).

Chowhan "Scale-up of the Aqueous Film Coating Process" in *Proceedings of the Pharm. Tech. Conference '86*, Sep. 16–18, 1986 Aster Publishing, Springfield, OR; pp. 264–279.

*Primary Examiner*—Shrive Beck
*Assistant Examiner*—Terry J. Owens
*Attorney, Agent, or Firm*—Philip E. Hansen; Paul E. Dupont

[57] ABSTRACT

A process for spray-coating tablets and the like utilizing only an acrylate enteric polymer and plasticizer in water is disclosed. The process can be practiced on a commercial scale and requires no antiadherent in the coating formulation. The process comprises providing inlet air having a dew point below about 10° C. and a temperature between 35° and 60° C.

18 Claims, No Drawings

AQUEOUS SPRAY-COATING PROCESS

This is a continuation of copending application Ser. No. 07/380048 filed on July 14, 1989, now abandoned.

BACKGROUND OF THE INVENTION

1. Field of the Invention

The invention relates to a process for the spray-coating of tablets, pills, and the like with a mixture of a 1:1 copolymer of ethyl acrylate and methacrylic acid, a plasticizer and water. The process may be used on a commercial scale and obviates the need for a glidant in the spray-coating suspension.

2. Information Disclosure

Patell, U.S. Pat. No. 4,775,536, describes the spray-coating of an 11-kg batch of 600 mg aspirin tablets with an aqueous suspension of Eudragit®L30D (a 1:1 copolymer of ethylacrylate and methacrylic acid), triethyl citrate, propylene glycol, antifoam emulsion, light mineral oil, sorbitan monolaurate and sorbitan monooleate. The tablets have been previously undercoated with a hydroxypropylmethylcellulose (HPMC) suspension to give strength to the tablet cores and to "prepare the tablets for enteric coating." After spraying with the enteric coating (Eudragit®), the tablets are immediately dusted with talc before applying the overcoat of HPMC to prevent sticking. Patell does not describe the humidity or air flow rate but the temperature is disclosed to be 70–75° C.

Ishii et al., Japanese Application 56/208155, describe in Application Example 1 the coating of an unspecified quantity of 110 mg tablets of undisclosed nature with an aqueous suspension of methacrylic acid-ethyl acrylate copolymer (Eudragit®L30D) and triacetin. An undercoating of a water-soluble cellulose film-forming component is required. The temperature, humidity, and volume of inlet air for the spray-coating process are not disclosed.

Dechesne et al. [*J. Pharm. Belg.* 37, 273–282 (1982)]describe the aqueous spray-coating of 100 mg tablets of acetylsalicylic acid with Eudragit®L30D, plasticizer, and talc. The plasticizer is triacetin or diethylphthalate and the coating is carried out in 2.7 kg batches. The authors do not describe the coating of aspirin without talc; however, they do describe experiments carried out with a placebo tablet coated With and without talc:

"-in the absence of a filling substance, one equally obtains good gastroresistance although the films seem more fragile. Moreover, the appearance of the coating is clearly less appealing."

The coating process is carried out in a standard 40 cm pan at 30°, 35° and 40° C. with an unspecified volume of inlet air. The dew-point of the inlet air is not described but the description of the equipment utilized does not include a dehumidifying apparatus of any sort.

Lehmann [Acta Pharmaceutica Technologica 31, 96–106(1985)]describes the use of Eudragit®L30D for the enteric coating of tablets. He states:

"First the pigment suspension is prepared in the usual manner. If a gastric-resistant primary layer without coloring is to be prepared, it is advisable, in place of the pigment suspension, to suspend 50 g of talc as an antiadherent in 800 g of water and to add the redispersion [of Eudragit]. As a plasticizer, which is absolutely necessary for flawless coating, 10% PEG, calculated on the basis of polymer substance, was added to the foregoing redispersion so that the 600 g of dry substance consisted of 545 g of polymer powder and 55 g of PEG. Triacetin or triethyl citrate may also employed as the plasticizer."

In a recent textbook on coating technology Lehmann states: "Some solid additives acting as glidants are recommended in all coating formulations to reduce sticking effects during film formation and drying. The most effective additive in this respect is talc, which also improves the smoothness of the film." ["Chemistry and Application Properties of Polymethacrylate Coating Systems" in *Acueous Polyvmeric Coatinos for Pharmaceutical Dosaoe Forms*, J. W. McGinity ed., Marcel Dekker Inc., 1989, p.191]

The same textbook in a later chapter by Mehta ["Processing and Equipment Considerations for Aqueous Coatings" in *Aqueous Polymeric Coatings for Pharmaceutical Dosage Forms*, J.W. McGinity ed., Marcel Dekker Inc., 1989, p. 256–302]states: "The drying rate is determined by several parameters, including the latent heat of vaporization, the surface area of the material being dried, the relative humidity of the incoming drying air, the velocity and direction of the airstream, and the geometry of the drying chamber. For the most part, these are established by the choice of coating equipment and are therefore not easily varied. It is these parameters that dictate the maximum drying ability of the system. Certainly, it would be impossible to dry more solvent than the drying air can accept or to dry it any faster than it can be heated to its rapid transition temperature. It is important to determine and understand the physical limitations of the coating system dictated by these factors, and work within them. It is probably wise to monitor the inlet air temperature, the outlet air temperature, the surface bed temperature, and the spray rate.

"The effect of moisture, also known as the 'weather effect,' has been discussed in the literature [7]. It is a known fact that the heat content of moist air is higher than that of dry air. A thermodynamic model for aqueous film coating [8]may enable prediction of the behavior of a tablet coating process under different environmental conditions. However, the variation in heat content could result in different release profiles, depending on the solvents and types of polymeric systems used. Residual water in the coating layers may affect the film forming process. It is therefore recommended that the effect of ambient air dew points be examined as a part of the scale-up program in any coating operations."

Although Mehta recognizes that the dew point of the process air is a consideration in the practice of the film-coating process, he does not suggest modulating the dew point of the process air. The thermodynamic model to which Mehta refers is that of Ebey.

Ebey [*Pharmaceutical Technology* 11, 40–50 (1987)]proposes a thermodynamic model for aqueous film coating. The application of his mathematical model allows one to take one set of conditions (spray rate, air temperature, flow rate, and relative humidity) that have provided an empirically successful coating process and from them determine what new set of conditions would be similarly successful. An example is provided wherein an inlet air temperature increase of 11° C. is calculated to provide a constant coating efficiency as the inlet air humidity is raised from 25 grains per pound to 125 grains per pound. The discussion and conclusion states, "the process curves in FIG. 4 show how variations in the humidity of the inlet air can be accounted for by changes in the temperature of the inlet air ... Humidity can also be offset by either increasing the flow rate of the inlet air or decreasing the rate of solution delivery as shown in FIGS. 5 and 6." Like Mehta, Ebey does not suggest modulating humidity but rather modulating the other parameters to offset the effects of ambient humidity.

Reiland et al. [*Drug Development and Industrial Pharmacy* 9, 945-958 (1983)] proposes a similar thermodynamic model to that of Ebey.

It has now been surprisingly discovered that the presence of talc or a similar glidant is not necessary for the successful application of an Eudragit ®L30D enteric coat to commercial quantities of tablets—provided that the dew point of the process or inlet air is maintained below about 10° C.

Talc in the coating formulation—as recommended by the manufacturer and the art—gives rise to a major process complication: if not stirred, it tends to settle out. Latex dispersions such as Eudragit ®L30D do not withstand vigorous stirring; as a result talc settles out in the hoses and nozzles used for spray-coating. Frequent and extensive clean-up, while necessary and recommended, do not wholly avoid the problem and blockage followed by process interruption occurs nonetheless. On a commercial scale interruption is expensive, time-consuming, and can frequently affect product quality.

The elimination of talc or other glidants from the spray-coating dispersion would seem desirable. In fact, it has been found that the simple elimination of glidant will, on occasion, provide acceptable, coated tablets when the process is carried out on a small enough scale. The relatively small mass of tablets pressing together and the very high ratio of the volume of process air to the surface area of the tablets are apparently sufficient to offset the tackiness of the coat.

However, the simple elimination of talc results in severe sticking of tablets to each other and to the coating pan when coating is attempted on a commercial scale. By commercial scale is meant the processing of batches of tablets of a total weight of 140 kg or more. The sticking of the tablets not only results in an inefficient process but, more importantly, produces an unacceptably high proportion of tablets that fail the standard USP test for enteric coating.

If one takes the thermodynamic models that are available and applies them to the problem of setting parameters for a commercial scale coating process, one quickly concludes that, according to the model, there is little to be gained by providing process air with a dew point below 10° C. Referring to a standard psychrometric chart such as may be found in *Van Nostrand's Scientific Encyclopedia*, 6th Edition, page 2348, it can be seen that taking air with a dew point temperature of 10° C. and warming it to 30° C. (the minimum process temperature proposed for Eudragit ®L30D) lowers the relative humidity below 1%. Further reductions in relative humidity do not significantly alter the amount of water that a given volume of air can carry. Thus air at 30° C. can take up about 25g of water per kg of dry air if it is at 1% relative humidity (dew point 10° C.) at the start and no more than 25.5g if it is absolutely dry (dew point below −5° C.). For this reason the art focuses on the temperature and volume of the process air rather than on achieving very low relative humidity.

It has now been surprisingly found that the reduction in dew point of the process air below 10° C. provides a significant improvement in the process of spray-coating, allowing one to eliminate an antiadherent from the commercial formulation.

SUMMARY OF THE INVENTION

The invention provides a process for the enteric coating of commercial quantities of pharmaceutical dosage forms with an aqueous dispersion of a 1:1 copolymer of ethyl acrylate and methacrylic acid of mean molecular weight 250,000 and a plasticizer without need for an tiadherent, such as talc, or other additives. The dosage forms individually weigh between about 60 mg and about 1500 mg. The improvement that allows th elimination of antiadherent in a conventional spray-coating process comprises providing inlet air having a dew point below about 10° C. and a temperature between about 35° and about 60° C.

A 30% aqueous dispersion of the 1:1 copolymer of ethyl acrylate and methacrylic acid is commercially available from Rohm Pharma (West Germany) under the tradename Eudragit ®L30D. Examples of plasticizers include polyethylene glycols, propylene glycol, citrate esters, phthalate esters, and, preferably, triacetin.

Both the volume and the dew point of the inlet air are important to the success of the commercial-scale coating process. The dew point must be below about 10° C. and preferably is below about 5° C. The volume will be a function of the size of the batch being coated, the rate of spraying, the amount of water in the dispersion being sprayed, and to some extent the configuration of the coating pan being used. We have found that utilizing a procedure described by Z. Chowhan ("Scale-up of the Aqueous Film-Coating Process", Proceedings of the Pharm. Tech. Conf. 1986, 264-279) one can calculate a theoretical flow rate of inlet air for the parameters in a given coating operation; this calculated flow rate is then multiplied by a factor of not less than two nor more than four to provide a reasonable range of operating flow rates for the practice of our invention. Within this range one can adjust the flow rate to optimize conditions. One could also operate at flow rates greater than those suggested above, but providing excessive amounts of dried, heated air would be diseconomic in a commercial process, and at some point the spray-coating process would become unsatisfactory because the latex would dry before it had a chance to coalesce on the surface of the object being coated.

The temperature of the inlet air may be between about 35° C. and about 60° C., preferably between 40° and 50° C.

An aqueous dispersion containing about 20% solids may be applied at spray rates between 100 and 400 g/min. The spray rate may be proportionately higher for higher solids loading and lower for more dilute dispersions. Spray rates lower than 100 g/min are operable in the invention but result in processing times that become undesirably long for commercial production.

The process may be carried out utilizing spray-coating equipment well-known in the art. Typically the coating can be carried out in a perforated pan such as those manufactured under the trade names of Accela-Cota ® and HiCoater ®. The dispersion is applied through one or more spray nozzles. The inlet air is provided at the volume specified by the coating pan manufacturer: thus the calculations described above will provide an indication of the size coating pan that should be used.

Inlet air may be dehumidified to the very low levels needed for the practice of the invention by a two-stage process involving chilling followed by passage though silica gel. A commercially available apparatus that accomplishes the necessary second stage dehumidification for 2000 cfm of air is available from Airflow Company (Gaithersburg, MD, USA) as a "Dryomatic Model RC 2000."

EXAMPLE 1

A dispersion of 1.8 kg of triacetin in 21.0 kg of water was added with gentle agitation to 30.0 kg of Eudragit ®L30D that had been passed through a 100 mesh screen to remove agglomerates. The dispersion was gently agitated during coating.

140 kg of 405 mg tablets containing 325 mg of aspirin was placed in a 48-inch Accela-Cota pan and rotated at 5.5 to 6.5 rpm. Inlet air having $-10°$ C. dew point was provided at 2000 cfm and 40° to 50° C. The dispersion of Eudragit and triacetin was applied through two Graco air guns equipped with 1.04 mm nozzles located 90° to the rolling tablet bed and 14 to 15 inches away at a combined application rate of 360 mL/min. The total coating time was 2.75 hours to apply a coating of about 28 mg dry weight per tablet.

The tablets were coated with a color overcoat of hydroxypropylmethylcellulose (6.21 mg/tablet), triacetin (1.24 mg), titanium dioxide(0.62 mg), FD&C Yellow #6 lake dye (0.004 mg) and D & C yellow #10 lake dye (0/02 mg), polished with carnauba wax, and printed with a pharmaceutically acceptable printing ink.

EXAMPLE 2

A process exactly analogous to that of example 1 was used. Two changes were made: the dew point of the inlet air was $1.5 \pm 1.5°$ C. and the spray rate was 294 mL/min resulting in a coating time of three hours.

EXAMPLE 3

A process exactly analogous to that of example 1 was used. The dew point of the inlet air was $5 \pm 2°$ C. and the spray rate was 272 mL/min resulting in a coating time of 3.25 hours.

EXAMPLE 4

A process exactly analogous to that of example 1 was used. The dew point of the inlet air was $10°$ C. $\pm 2°$ C. and the spray rate was 220 mL/min resulting in a coating time of 4.3 hours.

EXAMPLE 5

A process exactly analogous to that of example 1 was used. The dew point of the inlet air was 20° C. and the spray rate was 120 mL/min, which would have resulted in a coating time of 7.5 hours, but the process was terminated at two hours because the tablets were sticking too badly to continue.

The tablets of the foregoing examples were tested according to the procedure of USP XXI 1245 in 0.1 M HCL. The tablets of examples 1 through 4 passed; the tablets of example 5 failed.

We claim:

1. A method of preventing pharmaceutical dosage forms from adhering during spray coating, comprising: spraying said pharmaceutical dosage forms in the absence of glidant with a mixture consisting essentially of a one to one copolymer of ethyl acrylate and methacrylic acid and a plasticizer in air having an inlet dew point below about 10° C. and an inlet temperature between about 35° C. and about 60° C.

2. A method according to claim 1 wherein said dosage forms individually weight from about 60 mg to about 1500 mg.

3. A method according to claim 2 wherein the dew point of said inlet air is below about 5° C. and the temperature of said inlet air is between about 40° C. and about 50 ° C.

4. A method according to claim 2 wherein the total weight of said pharmaceutical dosage forms being spray-coated in one batch is greater than 140 kg.

5. A method of preventing tablets from adhering during spray coating, comprising: spraying said tablets in the absence of a glidant with a mixture consisting essentially of a one to one copolymer of ethyl acrylate and methacrylic acid and a plasticizer in air having an inlet dew point below about 10° C. and an inlet temperature between about 35° C. and about 60° C.

6. A method according claim 5 wherein said tablets individually weigh from about 60 mg to about 1500 mg.

7. A method according to claim 6 wherein the total weight of said tablets being spray-coated in one batch is greater than 140 kg.

8. A method according to claim 7 wherein said tablets contain aspirin as the active ingredient.

9. A method according to claim 8 wherein said tablets individually weigh from about 60 to about 650 mg.

10. A method according to claim 5 wherein said tablets contain aspirin as the active ingredient.

11. A method according to claim 10 wherein said tablets individually weigh from about 60 to about 650 mg.

12. A method according to claim 5 wherein the dew point of said inlet air is below about 5° C. and said inlet air is from about 40° C. to about 50° C.

13. A method according to claim 12 wherein the total weight of said tablets being aqueous spray-coated in one batch is greater than 140 kg.

14. A method according to claim 13 wherein said tablets contain aspirin as the active ingredient.

15. A method according to claim 14 wherein said plasticizer in said spray-coating mixture is triacetin.

16. A method according to claim 15 wherein said tablets weigh individually from about 60 mg to about 650 mg.

17. A method according to claim 16 wherein said tablets contain individually about 325 mg of aspirin.

18. A method of preventing batches of aspirin tablets containing more than 140 kg of tablets from adhering during spray coating, comprising: spraying said batches of tablets in the absence of a glidant with a mixture consisting essentially of a one to one copolymer of ethyl acrylate and methacrylic acid and a plasticizer in air having an inlet dew point below about 10° C. and an inlet temperature between about 35° C. and about 60° C.

* * * * *